US011191514B2

(12) United States Patent
Boutry

(10) Patent No.: US 11,191,514 B2
(45) Date of Patent: Dec. 7, 2021

(54) METHOD FOR ESTIMATING THE DOSE ADMINISTERED BY A RADIOLOGY SYSTEM

(71) Applicant: D.R.E.A.M Développement et Recherches En Applications Médicales, Toulouse (FR)

(72) Inventor: Christine Boutry, Mervilla (FR)

(73) Assignee: D.R.E.A.M DÉVELOPPEMENT ET RECHERCHES EN APPLICATIONS MÉDICALES, Toulouse (FR)

(*) Notice: Subject to any disclaimer, the term of this patent is extended or adjusted under 35 U.S.C. 154(b) by 75 days.

(21) Appl. No.: 16/494,049

(22) PCT Filed: Mar. 13, 2018

(86) PCT No.: PCT/FR2018/050583
§ 371 (c)(1),
(2) Date: Sep. 13, 2019

(87) PCT Pub. No.: WO2018/167422
PCT Pub. Date: Sep. 20, 2018

(65) Prior Publication Data
US 2021/0121151 A1    Apr. 29, 2021

(30) Foreign Application Priority Data
Mar. 16, 2017    (FR) .................................... 1752153

(51) Int. Cl.
H05G 1/42        (2006.01)
A61B 6/00        (2006.01)
(52) U.S. Cl.
CPC .......... A61B 6/542 (2013.01); A61B 6/5282 (2013.01); A61B 6/582 (2013.01)

(58) Field of Classification Search
CPC .......... A61N 2005/1094; A61N 5/1075; A61N 2005/1054; A61N 5/1031; A61N 5/1049;
(Continued)

(56) References Cited

U.S. PATENT DOCUMENTS 10,272,268 B2 *  4/2019  Boutry-Duthil ..... A61N 5/1075
2008/0292055 A1 * 11/2008  Boone .................. G01T 1/02
                                                  378/97
(Continued)

FOREIGN PATENT DOCUMENTS

EP      0979027 A2      2/2000
FR      2849697 A1      7/2004
WO      2015/177343 A1  11/2015

OTHER PUBLICATIONS

Société Française De Physique Médicale, "Dosimétrie des explorations diagnostiques en radiologie", Société Française de Physique Médicale, Dec. 2014, pp. 1-86, Rapport S.F.P.M. N° 30, Centre Antoine Béclère, 45 rue des Saints Pères, 75270 Paris Cedex 06.
(Continued)

Primary Examiner — Irakli Kiknadze
(74) Attorney, Agent, or Firm — Pearne & Gordon LLP

(57) ABSTRACT

The invention relates to a method for estimating a dose administered by a radiology system provided with an X-ray source and a flat surface sensor, wherein (a) an X-ray image of the patient is acquired by the flat surface sensor; (b) the grey level of the pixel is determined at the centre of the X-ray image; (c) the kerma K is calculated, on the patient's entrance from the grey level, from the electrical charge passing through the X-ray tube during the patient's exposure time, the thickness of the patient's body along the axis of the X-ray beam and the distance between the X-ray source and the patient. This method of estimating dose can significantly reduce the margin of error on the dose administered.

5 Claims, 4 Drawing Sheets

(58) Field of Classification Search
CPC ...... A61N 5/1071; G16B 45/00; G16B 50/00; G16B 5/00; G16H 40/63; G16H 50/50; A61B 6/10; A61B 6/107; A61B 6/542; A61B 6/583; A61B 6/027; A61B 6/032; A61B 6/0487; A61B 6/06; A61B 6/4028; A61B 6/4035; A61B 6/4042; A61B 6/405; A61B 6/4085; A61B 6/4241; A61B 86/4275; A61B 6/4441; A61B 6/4488; A61B 6/482; A61B 6/484; A61B 6/488; A61B 6/508; A61B 6/5288; A61B 6/5282; A61B 6/582; A61B 6/00; A61B 6/5235; A61B 6/544; A61B 5/1032; A61B 5/1079; A61B 5/318; A61B 5/441; A61B 5/445; A61B 5/4848; A61B 5/7275; A61B 6/14; A61B 6/4233; A61B 6/481; A61B 6/503; A61B 6/5229; G09B 23/286; G01T 1/02; G01T 1/2985; G01T 1/1663; G06T 2207/20224; G06T 5/002; G06T 7/0012; G06T 19/006; G06T 2207/10024; G06T 2207/10081; G06T 2207/20221; G06T 2207/30004; G06T 2207/30088; G06T 2210/41; G06T 7/0014; G06T 7/11; G06T 7/174; G06T 7/30; G06T 7/62; G06T 7/90; G01N 2223/1016; G01N 2223/401; G01N 23/04; G01N 23/223; H01L 27/14663; H01L 31/08; H04N 5/32; H05G 1/46; H05G 1/60; H05G 1/30; H05G 1/32; H05G 1/38; H05G 1/44; G21K 1/046; G21K 1/10; G21K 5/00; G06N 20/00

USPC ...................................... 378/7, 8, 62, 64, 97
See application file for complete search history.

(56) References Cited

U.S. PATENT DOCUMENTS

| | | | |
|---|---|---|---|
| 2015/0100290 A1* | 4/2015 | Falt | G16H 40/63 703/2 |
| 2018/0110493 A1* | 4/2018 | Golan | G01T 1/1647 |

OTHER PUBLICATIONS

Willi A. Kalender et al., "Generating and using patient-specific whole-body models for organ dose estimates in CT with increased accuracy: Feasibility and validation", Institute of Medical Physics, University of Erlangen-Nürnberg, Germany, 2014, pp. 925-933, Elsevier Ltd., Erlangen, Germany.
International Search Report for International Patent Application No. PCT/FR2018/050583, dated Jun. 25, 2018.
Written Opinion for International Patent Application No. PCT/FR2018/050583, dated Jun. 25, 2018.
Preliminary French Search Report for French Patent Application No. 17 52153, dated Aug. 22, 2017.

* cited by examiner

METHOD FOR ESTIMATING THE DOSE ADMINISTERED BY A RADIOLOGY SYSTEM

TECHNICAL FIELD

The present invention generally relates to the field of radiology and more particularly that of dosimetry in radiology.

PRIOR ART

The increase in the number of radiologic examinations (conventional radiography, scans, interventional radiology) undergone by the patients has become a major subject of public health. Indeed, exposure to ionising radiation induces deposits of energy in the matter and leads to radiobiological effects that can have serious consequences, of a deterministic nature (radiodermatitis for example) or stochastic nature (cancer for example). It is consequently essential to be able to ensure a precise evaluation as well as a follow-up of the doses of energy administered to patients over the course of time.

To date, there are primarily two solutions for estimating a dose administered in radiology. The first solution is to measure the product dose surface or PDS via an ion chamber at the output of the X-ray tube with determination of the input surface of this chamber. However, this measurement takes account only of the physical parameters of the tube, not the morphology of the patient. A second solution is to calculate the dose at the input (of the patient) according to the physical parameters of the tube and of the exposure geometry. However, this calculation is generally very imprecise, does take account of the morphology of the patient and does not make it possible to take account of the variations in geometry over time (scans or interventional radiology for example).

The reference dosimetric magnitudes shall be presented in a first step.

Generally, estimating doses in radiology calls upon a characteristic dosimetric magnitude of the beam, called Kerma (Kinetic Energy Released per unit Mass). The kerma is defined by:

$$K = \frac{dE_{tr}}{dm} \quad (1)$$

where $dE_{tr}$ is the total energy transferred (in the form of kinetic energy) of the X photons to the charged particles (electrons) in of volume of matter of mass dm. The kerma is expressed in $J \cdot kg^{-1} \cdot s^{-1}$ or, equivalently in $Gy \cdot s^{-1}$. The kerma is generally formed of two components: the collision kerma ($K_{col}$) and radiation kerma ($K_{rad}$) but in the energy range of the X photons for radiology the radiation kerma can be neglected in relation to collision kerma.

In conventional radiology, the kerma in the air can be expressed using exposure parameters of the X-ray tube. More precisely, the kerma in the air, at a given point P, $K_{air}(P)$, is proportional to the charge of the tube used, mAs, (i.e. the product of the intensity of the current passing through the tube by the exposure time) and the square of the accelerating voltage ($kV_p$) of the electrons in the tube. It is moreover inversely proportional to the square of the distance ($d_{FP}$) of the point in question at the core of the source and to a filtering factor (F) of the tube, or:

$$K_{air}(P) \propto \frac{mAs}{d_{FP}^2} \cdot \frac{(kV_p)^2}{F} \quad (2)$$

The dose absorbed represents the energy deposited locally per unit of mass dm. It is defined by:

$$D = \frac{d\varepsilon}{dm} \quad (3)$$

where $d\varepsilon$ is the energy deposited by ionising radiation (direct or indirect) into an element of matter of mass dm. It is expressed in $J \cdot kg^{-1}$ or, equivalently, in Gy.

As indicated hereinabove, the kerma K represents the energy transferred while the dose absorbed, D, represents the energy absorbed. As a general rule, the energy is not absorbed at the location where it is deposited due to the travel of the secondary electronic in the material. However, in the field of radiology, as the X photons X are low energy (energy less than 150 keV), the electronic balance is established at a shallow depth in the material and it is commonly admitted that D≈K.

A certain number of dosimetric magnitudes, called derivatives, are obtained from reference dosimetric magnitudes. This is in particular the standardised flow rate of kerma in air, noted as $nK_{air}$. This magnitude, also called the output of the tube, represents the kerma per unit of electrical charge passing in the tube and is therefore defined by:

$$nK_{air} = \frac{K_{air}}{mAs} \quad (4)$$

where $nK_{air}$ is expressed in $Gy \cdot (mAs)^{-1}$.

A detailed description of dosimetric magnitudes and of their relationships can be found in the report of the Société Françise de Physique Médicale, SFPM no. 30, December 2014, entitled "Dosimétrie des explorations diagnostiques en radiologie".

Different types of dosimeters have been considered in literature to estimate the dose absorbed during a radiological examination. In particular, application FR-A-2849697 proposes to use a network of crossed optical fibres coupled to a multichannel photomultiplier to measure a dose during an interventional radiological procedure. However, this device is complex and expensive, and does not make it possible to measure with accuracy the dose absorbed by the patient.

The purpose of the present invention is consequently to propose a method of measurement that is simple, inexpensive and that makes it possible to evaluate the dose absorbed by the patient with a margin of error that is substantially less than that of prior art.

DISCLOSURE OF THE INVENTION

The present invention is defined by a method of estimating the dose administered to a patient by a radiology system provided with a source of X rays and with a flat plate sensor, according to which:

(a) an X-ray image of the patient is acquired using the flat plate sensor;

(b) the gray scale is determined, NG, of the pixel at the centre of the X-ray image, corresponding to the intersection of the image with the axis of the X-ray beam;

(c) the kerma $K_e$ is calculated at the input of the patient from said gray scale, NG, from the electrical charge passing through the X-ray tube of the source, mAs, during the exposure time of the patient, from the thickness δ of the body of the patient along the axis of the X-ray beam and from the distance $d_i$ that separates the source of X rays from the patient.

The kerma at the input of the patient can then be calculated using the expression:

$$K_e = B\left(\frac{d_{ref}}{d_i}\right)^2 \left[a + b\ln\left(\frac{NG}{mAs} \cdot e^{\mu\delta} - c\right)\right] mAs$$

where B is a predetermined backscatter factor, $d_{ref}$ is a reference distance at which the dosimetry calibration is carried out, a, b, c are coefficients of a calibration law of the flow rate of kerma in the air at said reference distance and μ is the coefficient of attenuation of the X rays in water.

Advantageously, during a first calibration phase, is measured, for a plurality of amperage values of the tube and/or of the accelerating voltage and/or of the exposure time, on the one hand the flow rate of kerma in the air, $nK_{air}$, at said reference distance $d_{ref}$ using an absolute dosimeter and, on the other hand, the gray scale of the pixel at the centre of the X-ray image, standardised by the electrical charge passing through the X-ray tube, with the coefficients a, b, c being determined as those that best satisfy the relationship $nK_{air}$=a+b ln(NGn−c) for said plurality of values.

In a second calibration phase, water phantoms of different thicknesses x are then interposed between the source of X rays and the flat plate sensor, and the gray scale of the central pixel of the X-ray image is determined for each one of these thicknesses, NG(x), as well as the gray scale of this pixel in the absence of a phantom, NGn(0), for the same electrical charge passing through the X-ray tube, then the logarithmic ratios ln $$\frac{NGn(x)}{NGn(0)}$$

are calculated for the different thicknesses, and finally from this is deduced the coefficient of attenuation by linear regression on these logarithmic ratios.

According to an alternative, prior to the step (b), the background noise is removed from the X-ray image by subtracting therefrom an X-ray image acquired in the absence of irradiation, in order to obtain a de-noised X-ray image.

Furthermore, prior to the step (b) the variations in gain are advantageously corrected pixel-by-pixel using said de-noised image, in such a way as to obtain a de-noised image of a uniform intensity for a uniform irradiation of the flat plate sensor.

BRIEF DESCRIPTION OF THE DRAWINGS

Other characteristics and advantages of the invention shall appear when reading a preferred embodiment of the invention in reference to the accompanying figures among which.

DETAILED DISCLOSURE OF PARTICULAR EMBODIMENTS

The idea at the base of the invention is to evaluate the dose administered to a patient from the gray scale at the centre of the X-ray image. The term centre of the X-ray image means the point of intersection of the axis of the X-ray beam with the plane of the image.

The X-ray image is obtained by means of a flat plate sensor capable of detecting a low-energy incident X ray and to sample it both spatially and in intensity.

A distinction is made between direct conversion flat sensors and indirect conversation flat sensors. Direct conversion flat sensors use a photoconductive material (for example amorphous selenium) to directly convert the incident X ray into electrical charges which are collected by an array of TFT transistors. Indirect conversation flat sensors use the association of a scintillator and an active array of photodiodes (made of amorphous silicon), with the scintillator converting the X photons into optical photons and the active array converting the optical photons into electrical charges. The electrical charges thus generated are collected by an array of TFT transistors as in the direct conversion sensor.

The imaging system is comprised of a low-energy radiation source (keV) and of a flat plate sensor, associated with an acquisition system. The source and the flat plate sensor are mounted on two robot arms (not shown) and can be placed facing.

The robot arms can perform a rotation (generally of 360°) around a fixed point called isocentre.

The acquisition system receives the raw radiological image from the flat plate sensor, in other words the values of the intensity of the different pixels. It first of all carries out a correction of the offset inhomogeneities of the flat plate sensor, pixel by pixel. More precisely, it subtracts from each pixel the intensity detected in the absence of irradiation called DF (Dark Field) intensity. In other terms, an X-ray image obtained without irradiation is subtracted from the raw radiological image in such a way as to obtain a de-noised image. It then corrects, the gain inhomogeneities, pixel by pixel, due to the variations in the parameters of the amplifiers in the detection array, in such a way that the de-noised image is of uniform intensity for a uniform irradiation of the flat plate sensor.

Such an acquisition system and the gain corrections that it applies are well known in prior art.

The method of dosimetry according to the present invention supposes carrying out beforehand steps of calibration which are described hereinafter in relation with FIGS. 1A and 1B.

Figure 1A:
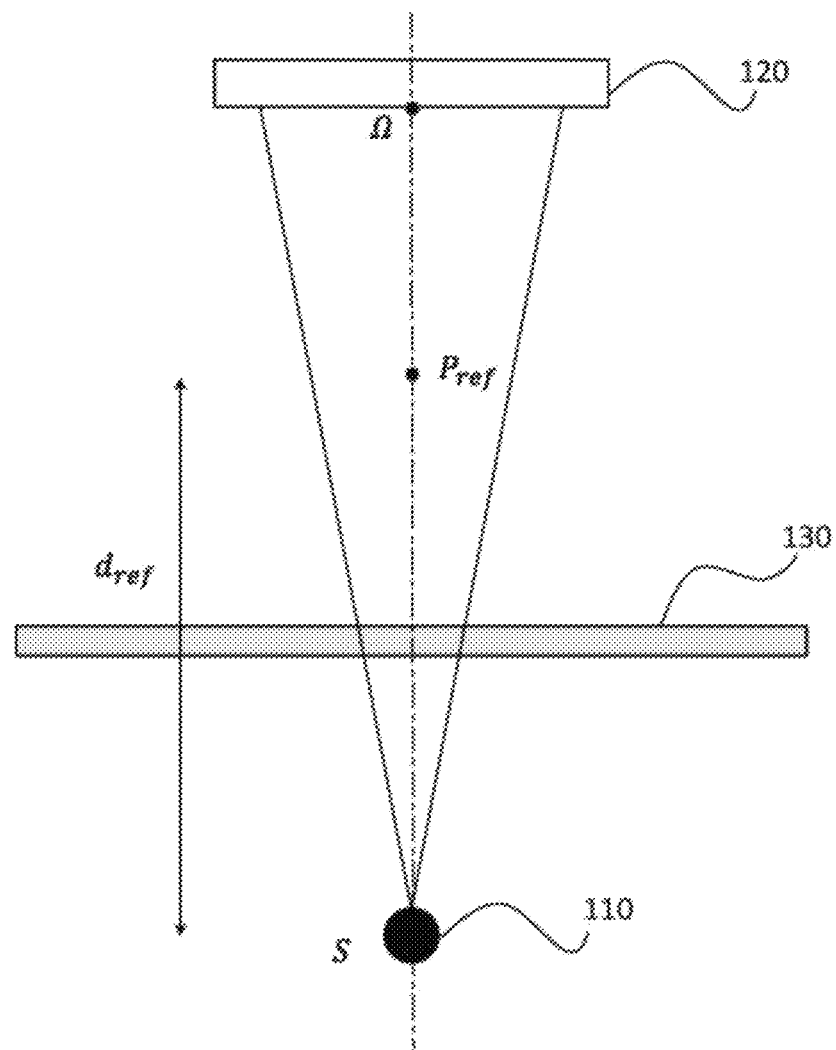
FIG. 1A diagrammatically shows a first configuration of a radiology system during a first step of calibration of the method of dosimetry according to the invention.

FIG. 1A diagrammatically shows a first configuration of a radiology system during a first step of calibration of the dosimetry method.

The source of X rays has been designated by 110 and the flat plate sensor by 120. The source and the flat plate sensor are mounted facing on a robot arm. A table has been illustrated in 130 on which the patient can be lying down during the intervention. It will however be understood that this table is optional and that is can furthermore be replaced with another type of support that makes it possible to position the patient. It shall be assumed in what follows that the table has a low attenuation to low-energy X rays (keV), in such a way that its influence can be neglected in a first approximation.

During the first step of calibration, the measurements are taken "bare flame", i.e. without attenuation between the source and the flat plate sensor, in other words in the absence of a patient or calibration phantom.

It has been shown that the flow rate of kerma in air, measured at a reference distance, $d_{ref}$, from the source, could be expressed in the form:

$$nK_{air} = a + b \ln(NGn - c) \tag{5}$$

where NGn is the gray scale of the pixel at the centre, $\Omega$, of the X-ray image (supplied by the acquisition system), standardised by the electrical charge passing in the tube, or:

$$NG_n = \frac{NG}{mAs} \tag{6}$$

where NG is the gray scale at the centre of the X-ray image.

The coefficients a, b, c present in the calibration law (5) are constants that depend only on the characteristics of the radiology system (source, flat plate sensor).

The coefficients a, b, c are calculated from a plurality of measurements of standardised gray scales (NGn) for different flow rates of kerma ($nK_{air}$), by minimising the quadratic error between the measurements and the curve that represents the calibration law (curve fitting). The various standardised flow rates of kerma can be obtained for example by varying the amperage of the tube, the accelerating voltage and/or the exposure time.

It is understood that the calibration law (5) makes it possible to connect a gray scale of the X-ray image and to a flow rate of kerma measured in the air, at a reference value.

The measurement of the flow rate of kerma at the reference distance can be carried out for example by means of a dose measuring device such as the NOMEX™ kit from the company PTW, having benefitted from a primary calibration.

Figure 1B:
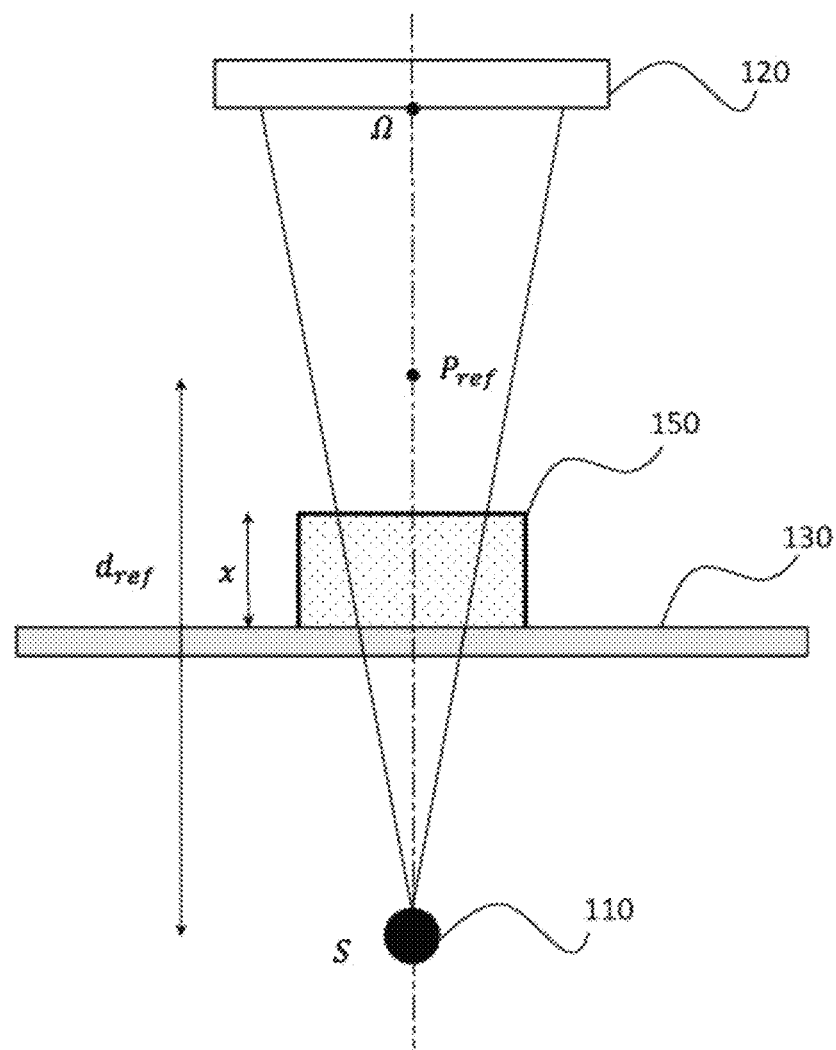
FIG. 1B diagrammatically shows a second configuration of a radiology system during a second step of calibration of the method of dosimetry according to the invention.

FIG. 1B diagrammatically shows a second configuration of a radiology system during a second step of calibration of the method of dosimetry.

This second configuration is distinguished from the first by the interposition of a water phantom, 150, between the source and the flat plate sensor, with the other elements of the radiology system remaining identical.

If x denotes the thickness of the phantom in the axis of the beam, the intensity I(x) of the beam that reaches the flat plate sensor at the centre of the X-ray image, after having passed through the water phantom, is given by:

$$I(x) = I_0 e^{-\mu x} \tag{7}$$

where $\mu$ if the coefficient of attenuation of the beam in water and $I_0$ is the intensity of the beam at the centre of the X-ray image at bare flame (in the absence of a phantom). It can then be deduced therefrom:

$$NGn(x) = NGn(0) e^{-\mu x} \tag{8}$$

where NGn(x) and NGn(0) are the standardised gray scales of the pixel at the centre of the X-ray image, $\Omega$, respectively in the presence of a water phantom and at bare flame.

By using water phantoms of different thicknesses x and by calculating for these different thicknesses the logarithmic ratios ln $$\frac{NGn(x)}{NGn(0)},$$

it is possible to deduce therefrom by linear regression the coefficient of attenuation, $\mu$. Alternatively, it is possible to carry out the linear regression on the logarithmic ratios ln $$\frac{NG(x)}{NG(0)}$$

with the condition of measuring the gray scales NG(x) and NG(0) for the same electrical charge passing through the X-ray tube.

Figure 1C:
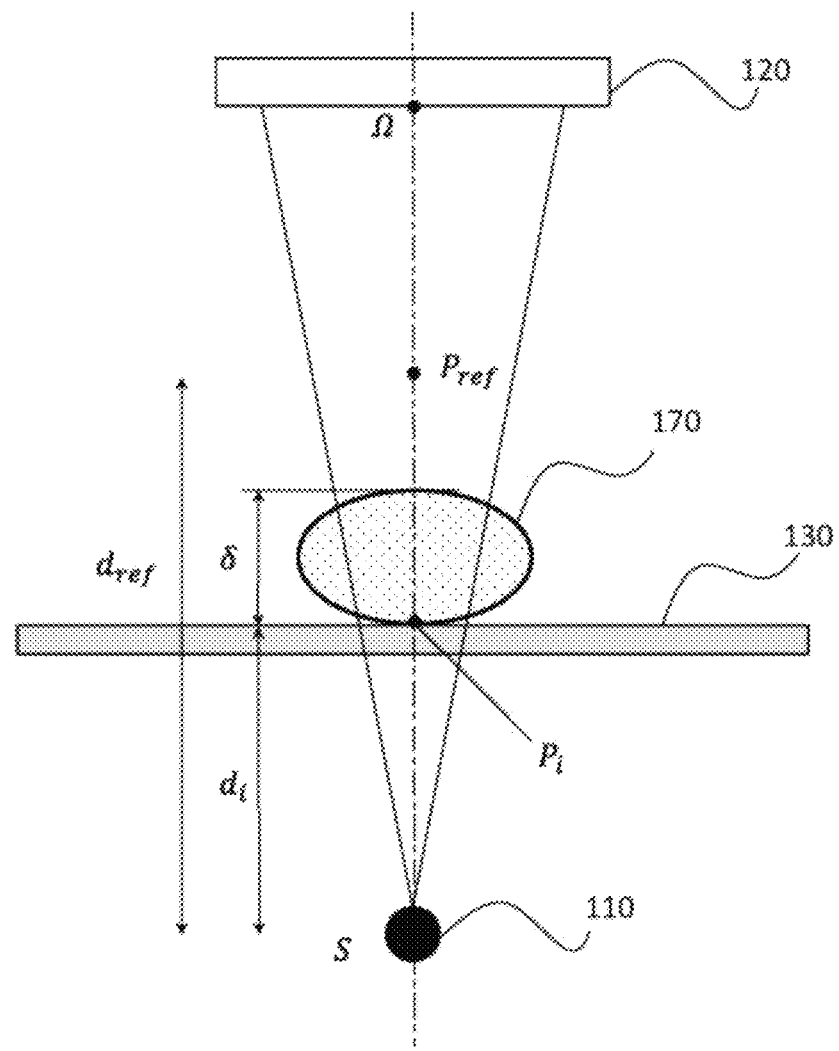
FIG. 1C diagrammatically shows a third configuration of a radiology system during the method of dosimetry according to the invention.

FIG. 1C diagrammatically shows a third configuration of the radiology system during the measurement of the dose administered to a patient, in accordance with an embodiment of the method of dosimetry according to the invention.

The third configuration is identical to the second configuration except for the difference that the patient 170 is arranged between the source of X rays and the flat plate sensor, instead of the water phantom.

As the human body is substantially comprised of water, it can be considered as a first approximation that the coefficient of attenuation of the X rays in the patient is equal to the coefficient of attenuation $\mu$ obtained in the second step of calibration.

From the gray scale of the pixel at the centre, $\Omega$, of the X-ray image of the patient, it is possible to determine the flow rate of kerma in the air, measured at the reference distance by:

$$nK_{air} = a + b \ln(NGn(0) - c) = a + b \ln(NGn(e)e^{\mu\delta} - c) \tag{9}$$

where NGn($\delta$) is the standardised gray scale of the pixel in question, $\delta$ being the thickness of the body of the patient in the axis of the beam.

The kerma in the air at the reference distance from the source is therefore given by:

$$K_{air} = [a + b \ln(NGn(\delta)e^{\mu\delta} - c)] mAs \tag{10}$$

where mAs is the electrical charge passing through the tube during the exposure time. It is possible to deduce therefrom the kerma, $K_i$, at the point of contact $P_i$ between the body of the patient and the table, on the axis of the beam. If $d_i$ denotes the distance between the source of X rays and the point of contact $P_i$, there is, according to the relationship (2):

$$K_i = K_{air} \cdot \left(\frac{d_{ref}}{d_i}\right)^2 \tag{11}$$

The kerma at the input of the patient, or dose administered to the patient, is the dosimetric magnitude in conventional radiology. It takes account of the dose, $K_i$, deposited by the incident beam on the surface of the patient but also the dose deposited by the backscattered radiation on the surface of the patient. It is generally admitted that the kerma at the input of the patient, $K_e$, is the product of the kerma due to the incident beam by a backscatter factor, B, or:

$$K_e = K_i \cdot B \tag{12}$$

Definitively, the kerma at the input of the patient can be expressed in the following form:

$$K_e = B\left(\frac{d_{ref}}{d_i}\right)^2 \left[a + b\ln\left(\frac{NG}{mAs} \cdot e^{\mu\delta} - c\right)\right] mAs \qquad (13)$$

It is reminded that the coefficients a, b, c are obtained by the first calibration step and that the coefficient of attenuation is obtained by the second calibration step. The electrical charge mAs passing through the tube is given as the product of the amperage passing through the tube and of the exposure time.

The thickness δ can be estimated using the corpulence of the patient. Alternatively, it can be estimated by means of a distance measuring device (equipped with an ultrasound or IR light sensor) integrated into the flat plate sensor. In this case, if $d_{SD}$ denotes the distance between the source and the detector (flat plate sensor) and z the distance between the flat plate sensor and the body of the patient according to the axis of the beam, measured by the device in question, there will simply be:

$$\delta = d_{SD} - d_i - z \qquad (14)$$

The backscatter factor is generally set to an average reference value (typically B is chosen equal to about 1.35), or taken from tables obtained by Monte-Carlo simulations forgiven beam qualities.

The gray scale of the pixel at the centre of the X-ray image, NG, is supplied by the flat plate sensor or, when the latter exists, by the acquisition system.

Figure 2:
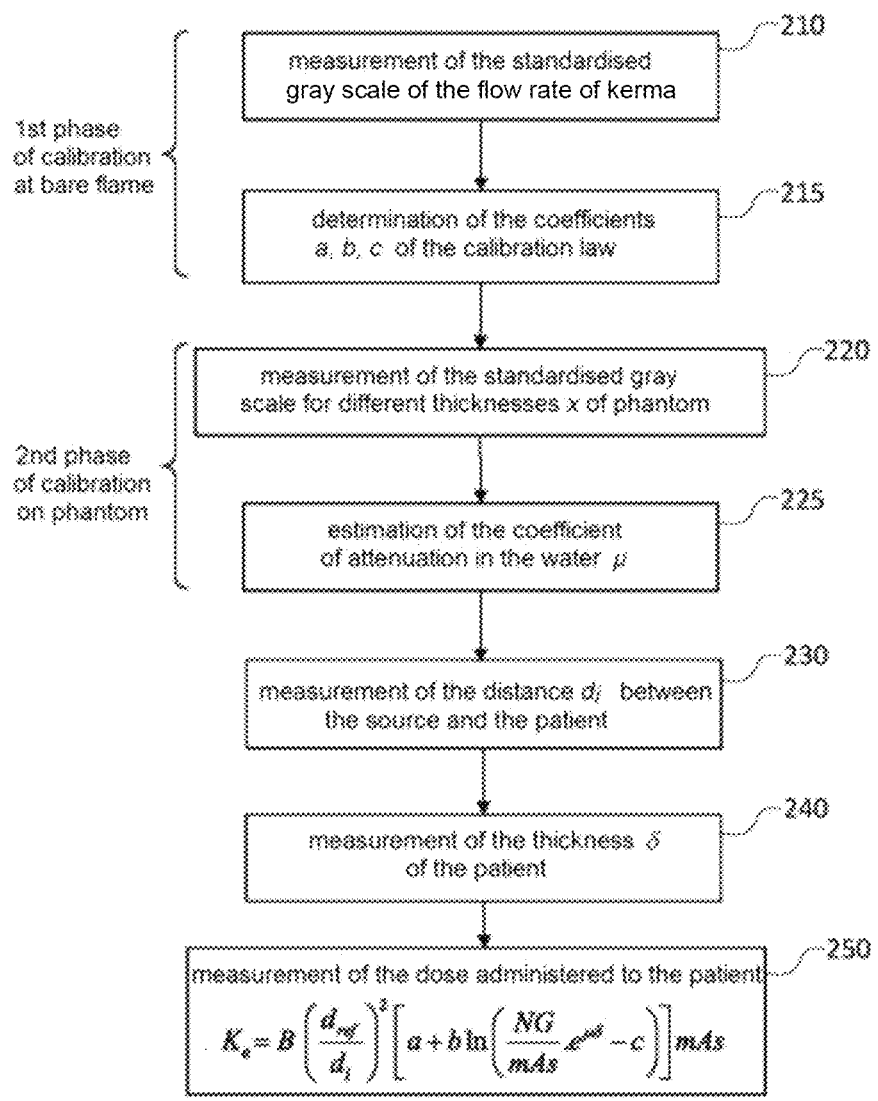
FIG. 2 diagrammatically shows a flow chart of the method of dosimetry for a radiology system, according to an embodiment of the invention.

FIG. 2 diagrammatically shows a flow chart of the method of dosimetry for a radiology system, according to an embodiment of the invention.

The steps 210 to 225 are calibration steps strictly speaking and carried out prior to the dose measuring strictly speaking.

In 210, in a configuration of the bare flame system, gray scale measurements are taken of the pixel at the centre, Ω, of the X-ray image, this for different values of amperage of the tube, of accelerating voltage and/or different exposure times, and the corresponding standardised gray scales are deduced therefrom, nNG.

Correlatively, using an absolute dosimeter, the kerma in the air is measured at a reference distance, $d_{ref}$, from the source of X rays, and the flow rate of kerma $nK_{air} = K_{air}/mAs$ is deduced therefrom, in the same conditions.

In the step 215, deduced from the measurements of $nK_{air}$ and nNG, are the coefficients of the calibration law (5).

In the step 220, the standardised gray scale is measured of the pixel at the centre, Ω, of the X-ray image, NGn, for water phantoms of different thicknesses x interposed between the source of X rays and the flat plate sensor, according to the second configuration of the radiology system.

In the step 225, deduced from the preceding measurements NGn, the coefficient of attenuation in water, μ, of the X rays emitted by the source.

In what follows the patient is interposed between the source and the flat plate sensor.

In the step 230, the distance $d_i$ is measured from the source to the patient along the axis of the beam.

In the step 240, the thickness δ is estimated or is measured from the patient along the axis of the beam.

Finally, in the step 250, the dose administered to the patient is estimated from the gray scale of the pixel at the centre of the X-ray image, NG, by means of the expression (13).

It has been shown that the doses measured using the gray scale NG were very close to the actual values, with a margin of error of at most about 5%-10%, which is substantially less than the margins of error generally observed for the methods of dosimetry of prior art (30%).

More generally, those skilled in the art will understand that after the calibration phase, the method disclosed hereinabove makes it possible to convert an X-ray image, in gray scale, supplied by an acquisition system, into a dose image. To do this, it is possible to replace in the expression (13), the thickness δ according to the axis of the beam with the thickness δ/cos θ where θ is the angle formed by the radius that joins the source and the pixel with the axis of the beam. The dose image thus calculated gives at each point the dose administered to the patient.

The invention claimed is:

1. Method for estimating a dose administered to a patient by a radiology system provided with a source of X rays and with a flat plate sensor, characterised in that:
   (a) an X-ray image of the patient is acquired using the flat plate sensor;
   (b) a gray scale is determined, NG, of the pixel at a centre of the X-ray image, corresponding to an intersection of the image with an axis of the X-ray beam;
   (c) a kerma $K_e$ is calculated at an input of the patient from said gray scale, NG, from an electrical charge passing through an X-ray tube of the source, mAs, during an exposure time of the patient, from a thickness δ of the body of the patient along the axis of the X-ray beam and from a distance $d_i$, that separates the source of X rays from the patient,
   wherein the kerma at the input of the patient is calculated using the expression:

$$K_e = B\left(\frac{d_{ref}}{d_i}\right)^2 \left[a + b\ln\left(\frac{NG}{mAs} \cdot e^{\mu\delta} - c\right)\right] mAs$$

where B is a predetermined backscatter factor, $d_{ref}$ is a reference distance at which the dosimetry calibration is carried out, a,b,c are coefficients of a calibration law of the flow rate of kerma in the air at said reference distance, and μ is the coefficient of attenuation of the X rays in water.

2. Method for estimating a dose administered to a patient according to claim 1, characterised in that, during a first calibration phase, is measured, for a plurality of amperage values of the tube and/or of the accelerating voltage and/or of the exposure time, on the one hand the flow rate of kerma in the air, $nK_{air}$, at said reference distance $d_{ref}$ using an absolute dosimeter and, on the other hand, the gray scale of the pixel at the centre of the X-ray image, standardised by the electrical charge passing through the X-ray tube, with the coefficients a, b, c being determined as those that best satisfy the relationship $nK_{air} = a + b\ln(NGn - c)$ for said plurality of values.

3. Method for estimating a dose according to claim 1, characterised in that, in a second calibration phase, water phantoms of different thicknesses x are interposed between the source of X rays and the flat plate sensor, in that for each one of these thicknesses the gray scale of the central pixel of the X-ray image is determined, NG(x), as well as the gray scale of this pixel in the absence of a phantom, NGn(0), for the same electrical charge passing through the X-ray tube, in that the logarithmic ratios ln $$\frac{NGn(x)}{NGn(0)}$$

are calculated for the different thicknesses, and in that the coefficient of attenuation is deduced therefrom by linear regression on these logarithmic ratios.

4. Method for estimating a dose according to claim 1, characterised in that, prior to the step (b), the background noise is removed from the X-ray image by subtracting therefrom an X-ray image acquired in the absence of irradiation, in order to obtain a de-noised X-ray image.

5. Method for estimating a dose according to claim 4, characterised in that, prior to the step (b), the variations in gain are corrected pixel-by-pixel from said de-noised image, in such a way as to obtain a de-noised image of a uniform intensity for a uniform irradiation of the flat plate sensor.

\* \* \* \* \*